(12) United States Patent
Grove et al.

(10) Patent No.: US 9,464,523 B1
(45) Date of Patent: Oct. 11, 2016

(54) RESERVOIR CHARACTERIZATION USING A WELL CORE

(71) Applicant: Schlumberger Technology Corporation, Sugar Land, TX (US)

(72) Inventors: Brenden Grove, Missouri City, TX (US); Jeremy Harvey, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/749,266

(22) Filed: Jun. 24, 2015

(51) Int. Cl.
*G01V 8/00* (2006.01)
*E21B 49/08* (2006.01)

(52) U.S. Cl.
CPC .................................. *E21B 49/088* (2013.01)

(58) Field of Classification Search
CPC ..................................................... E21B 49/088
USPC ........................................................... 250/255
See application file for complete search history.

(56) References Cited

U.S. PATENT DOCUMENTS

| 5,269,999 A | * | 12/1993 | Smesny | .................. | B29C 43/18 264/112 |
| 2009/0259446 A1 | * | 10/2009 | Zhang | ..................... | E21B 49/00 703/2 |

* cited by examiner

*Primary Examiner* — David Porta
*Assistant Examiner* — Edwin Gunberg
(74) *Attorney, Agent, or Firm* — Tuesday Kaasch

(57) ABSTRACT

A method for determining local permeability variations in a well core sample includes flowing a test fluid from an inflow surface of a core sample toward an exit surface of the core sample for a period of time, splitting the core sample along a splitting plane revealing an invasion depth of the test fluid and determining local permeability variations in the core sample using the invasion depth.

20 Claims, 4 Drawing Sheets

RESERVOIR CHARACTERIZATION USING A WELL CORE

BACKGROUND

This section provides background information to facilitate a better understanding of the various aspects of the disclosure. It should be understood that the statements in this section of this document are to be read in this light, and not as admissions of prior art.

Petroleum and other naturally occurring deposits of minerals or gas often reside in porous geologic formations deep in the Earth's crust. Once a formation of interest is located, a well is drilled from the Earth's surface down to the area of interest. Geologists or engineers often investigate the formation and the deposits therein by obtaining and analyzing a representative sample of rock. For example, a representative sample may be obtained using a rotary coring bit that removes a well core sample from the well. Once the well core sample has been transported to the surface, one or more properties of the well core sample are analyzed to evaluate the reservoir storage capacity (porosity), the flow potential (permeability) of the rock that makes up the formation, the composition of the fluids that reside in the formation, and to measure irreducible water content. These estimates are used to design and implement well completion; that is, to selectively produce certain economically attractive formations from among those accessible by the well.

SUMMARY

A method according to one or more embodiments includes flowing a test fluid from an inflow surface of a core sample toward an exit surface of the core sample for a period of time, splitting the core sample along a splitting plane revealing an invasion depth of the test fluid and determining local permeability variations in the core sample using the invasion depth. In accordance to some embodiments the inflow surface and the exit surface are the opposing axial ends of the core sample. In some embodiments, the inflow surface may be one of an outer circumferential surface and an inner surface of a channel and the exit surface is the other one of the outer surface and the inner surface.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Figure 1:
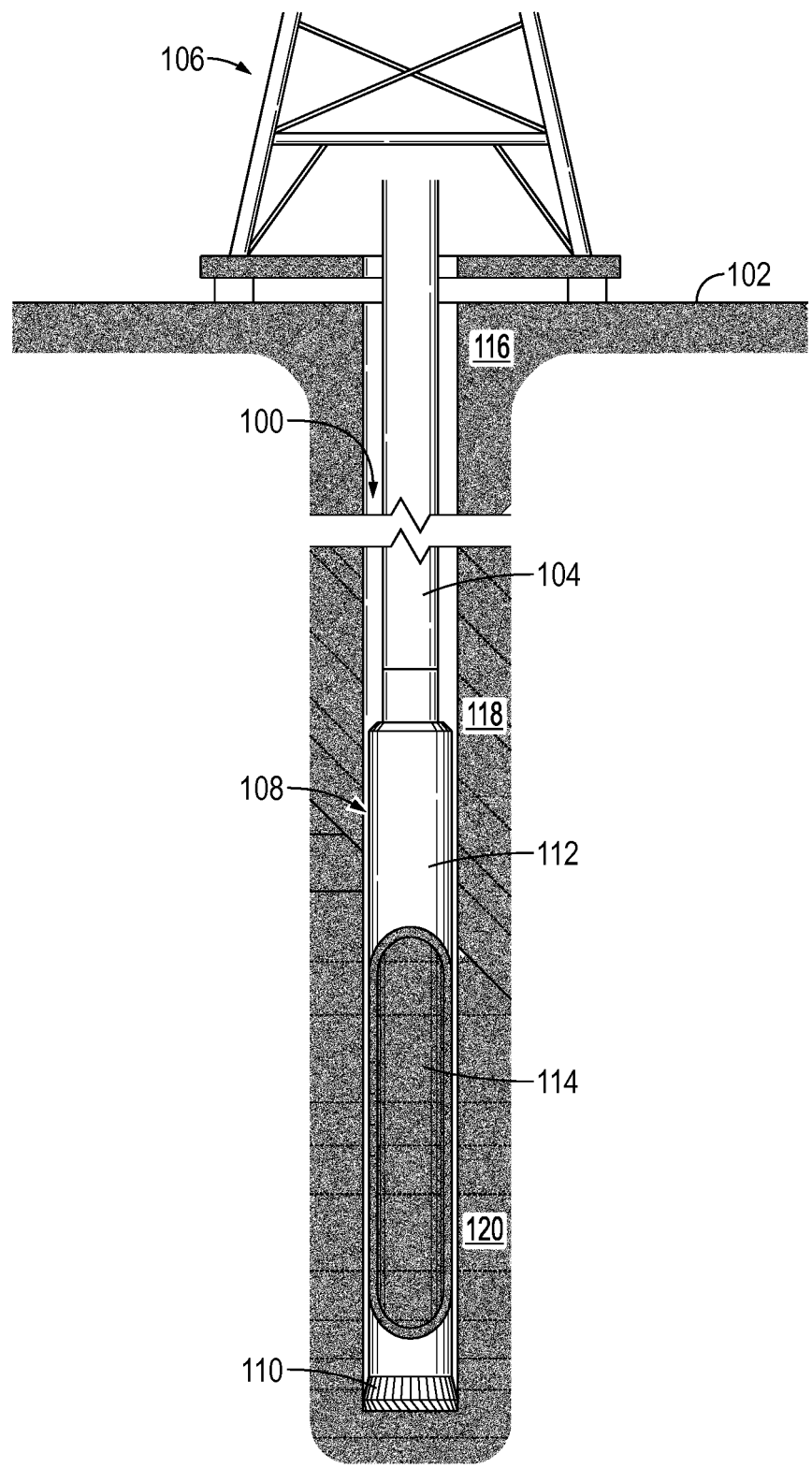
FIG. 1 illustrates a well system in accordance to one or more aspects of the disclosure.

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

FIG. 1 illustrates an example of obtaining well cores 114 from a wellbore 100 extending from earth surface 102. A coring tool 108 having a coring bit 110 and a barrel 112 is suspended in the wellbore from drilling rig 106 on a conveyance 104, illustrated as a tubular string in FIG. 1. The wellbore 100 may pass through one or more formations, such as formations 116 and 118, until a formation of interest, such as formation 120, is reached. In order to analyze one or more properties of the formation 120, a well core 114 can be collected using the coring tool 108.

The coring tool 108 is attached to conveyance 104 and lowered into the wellbore until the coring bit 110 bears against the formation 120. Rotation of the conveyance 104 causes the coring bit 110 to cut away a cylindrical area of the formation 120 to obtain well core 114. As the coring bit 110 works through the formation 120, the well core 114 is received and captured by the barrel 112. Well cores 114 can be of various diameters and lengths depending upon the size of the coring bit 110 and the consistency of the formation. Well cores may also be obtained by side wall coring. Conveyance 104 and coring tool 108 are tripped out of wellbore 100 and the well core 114 is retrieved at the surface for analysis.

After the well core 114 has been retrieved at the surface a determination of local permeability variations in the well core can be studied by flowing a test fluid 140 (see, FIGS. 4 and 5) into the well core parallel to bedding planes of the well core. In one or more aspects, the fluid may be a mineral oil or a water/brine mixture and the fluid may contain a fluorescent material or tracer. The tracer allows fluid inflow or invasion to be more easily detected. Tracers include dyes, such as a fluorescent dye, or radioactive particles. When using fluorescent dye, exposing the tested well core to ultraviolet light causes the phosphors contained in the dye to fluoresce and glow. The fluorescing fluid makes a flow field of the test fluid more visible. When using radioactive particles, various imaging techniques can be utilized to detect the location of the radioactive particles to reveal the flow field. In other aspects, other fluids or dyes can be used.

Figure 2:
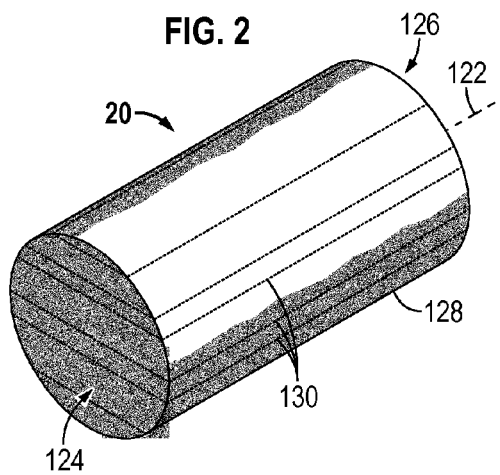
FIG. 2 illustrates a core sample with a primary bedding plane oriented parallel to its longitudinal axis according to one or more aspects of the disclosure.
Figure 3:
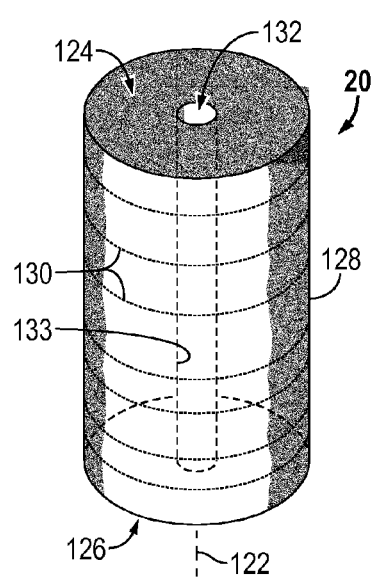
FIG. 3 illustrates a well core with the primary bedding plane oriented perpendicular to its longitudinal axis according to one or more aspects of the disclosure.

FIGS. 2 and 3 illustrate core samples 20 that have been obtained from the well core 114 and prepared for testing in accordance to one or more aspects of the disclosure. As will be understood by those skilled in the art with benefit of this disclosure, preparing a core sample for testing may include cleaning and obtaining one or more sections of the original well core 114 such that the size is appropriate for the test apparatus and so that the primary bedding planes are in a desired orientation. In some instances the core sample 20 may be the well core 114 as it was obtained from the wellbore. Each of the core samples 20 has a longitudinal axis 122, first and second axial ends 124, 126 and an outer circumferential surface 128. The core sample has a primary bedding plane generally shown by the striations denoted by the number 130 that are oriented relative to the longitudinal axis 122. The core sample may include one or more bedding planes. Core sample geometry may be, but need not be, cylindrical.

In FIG. 2 the bedding plane 130 is oriented substantially parallel to the longitudinal axis 122; as such test fluid is flowed axially into or through the core sample. In this orientation one of the first and the second axial ends 124, 126 is an inflow surface 125 and the other of the first and second axial ends is an outflow surface 127 during testing.

With reference to FIG. 3, test fluid must flow radially, or perpendicular to the longitudinal axis, for the test fluid to flow parallel to the bedding plane 130 direction. A passage or axial channel 132 is formed (e.g., drilled) axially into core sample 20 for example co-axial with the longitudinal axis 122. Channel 132 (central bore) may be formed partially through core sample 20 or extend axially from the first end 124 to the second end 126. During testing, one of the outer surface 128 and an inner surface 133 of the channel 132 is an inflow surface 125 and the other of the outer surface 128 and the inner surface 133 is the outflow or exit surface 127.

Figure 4:
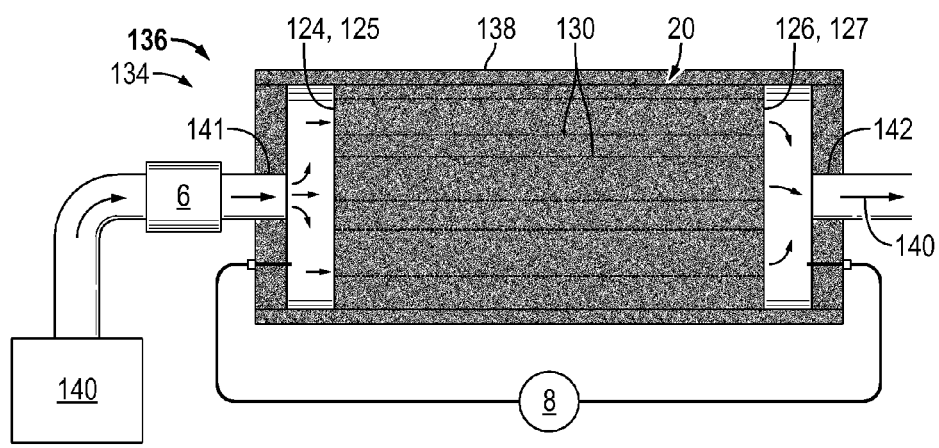
FIGS. 4 and 5 illustrate well core testing apparatus in accordance to one or more aspects of the disclosure.

FIG. 4 illustrates a test apparatus or system 134 for testing a core sample 20 as illustrated in FIG. 2. Core sample 20 is positioned in a flow chamber or test cell 136 with a lateral seal 138 confining the core sample 20 such that fluid flow is prevented from bypassing the core sample. A test fluid 140 is fed (e.g., pumped, fed under pressure) into the test cell 136 in communication with an inflow surface 125, i.e. the first end 124 in this example, of the core sample. For example a syringe pump may be utilized to apply the test fluid to the core sample. A flow meter 6 is illustrated at inlet 141 for measuring the flow rate of the test fluid 140 applied to the core sample. The outflow surface 127, i.e. the second end 126 in this example, of the core sample is in communication with an outlet 142 of the test cell. A differential pressure sensor 8 is illustrated connected between the inlet 141 and the outlet 142 to measure the differential pressure across the tested core sample 20. As will be understood by those skilled in the art with benefit of this disclosure, pressure may be applied to core sample 20 and/or test fluid 140 to simulate wellbore and reservoir conditions. Test fluid 140 may be applied or exposed to core sample 20 for a desired or specified period of time. In accordance to some embodiments, the flow of test fluid 140 is terminated when test fluid 140 breaks through the outflow surface 127 which is second end 126 in FIG. 4 example.

Figure 5:
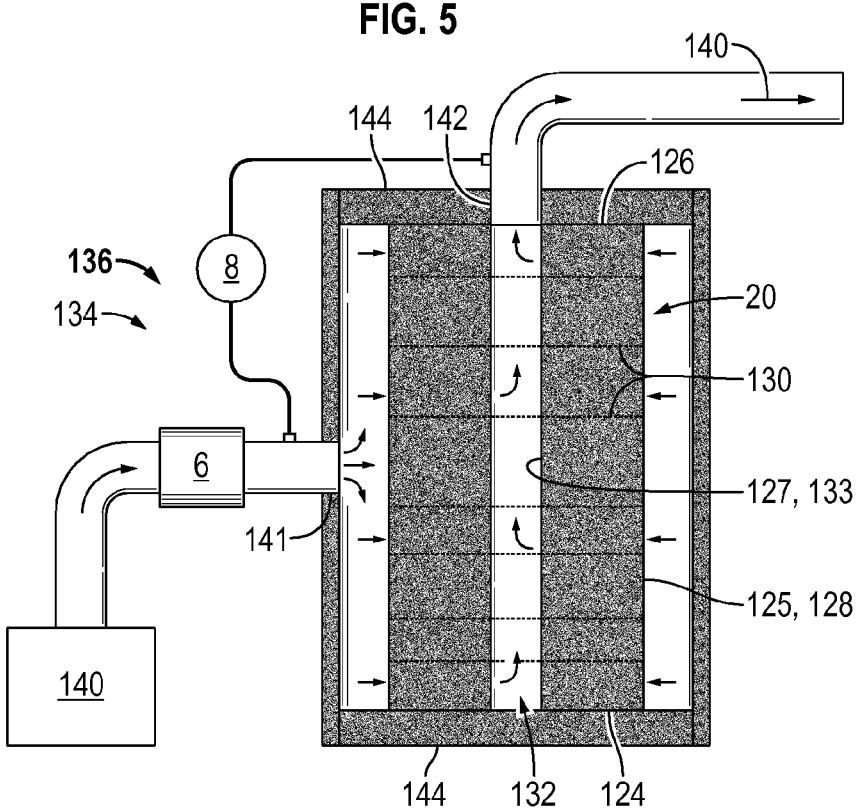

FIG. 5 illustrates a test apparatus or system 134 for testing a core sample 20 oriented for example as illustrated in FIG. 3. Core sample 20 is positioned in a flow chamber or test cell 136 such that the first and second ends 124, 126 are sealed and confined, for example as illustrated by seals 144, from inflow or outflow of test fluid 140. In the FIG. 5 illustration the test fluid 140 is applied at an inlet 141 to inflow surface 125, i.e., the outer surface 128 in this example, and the test fluid 140 flows parallel to the primary bedding plane 130 toward the outflow surface 127, which is inner surface 133 of channel 132 in this example. A flow meter 6 can measure the flow rate of the test fluid applied to the core sample. Channel 132 is in communication with outlet 142. A differential pressure sensor 8 is connected to measure the differential pressure across the tested core sample. In accordance to some embodiments, the test fluid 140 may be routed such that the inner surface 133 is the inflow surface and the outer surface 128 is the outflow surface. As will be understood by those skilled in the art with benefit of this disclosure, pressure may be applied to core sample 20 and/or test fluid 140 to simulate wellbore and reservoir conditions. Test fluid 140 may be applied to core sample 20 for a desired or specified period of time. In accordance to some embodiments, the flow of test fluid 140 is terminated when test fluid 140 breaks through the outflow surface 127 which is inner surface 133 in the FIG. 5 example.

Figure 6:
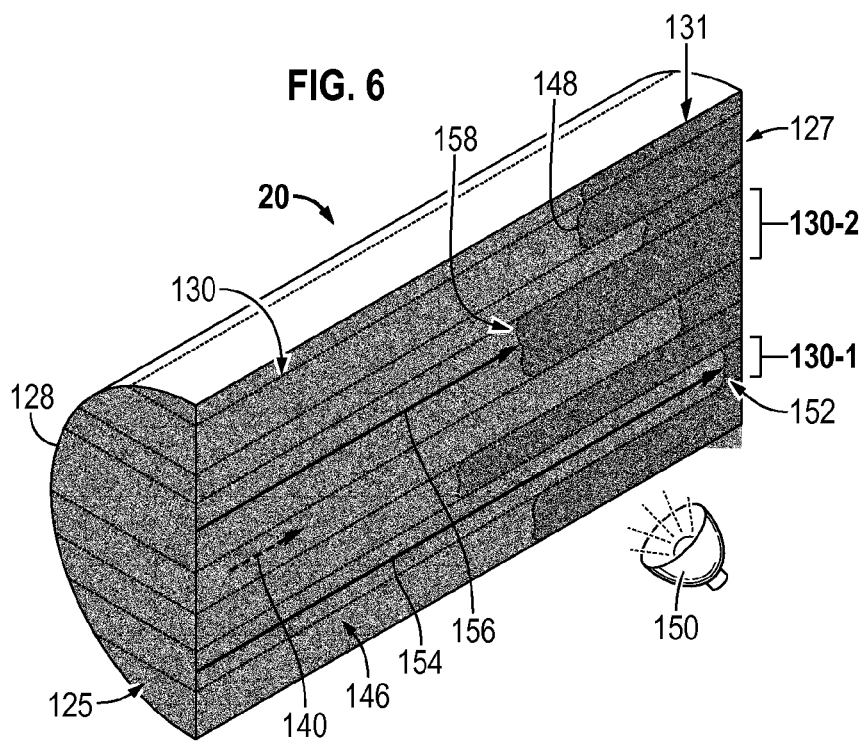
FIG. 6 illustrates a test fluid exposed core sample according to FIGS. 2 and 4 split along a plane perpendicular to the bedding plane according to one or more aspects of the disclosure.
Figure 7:
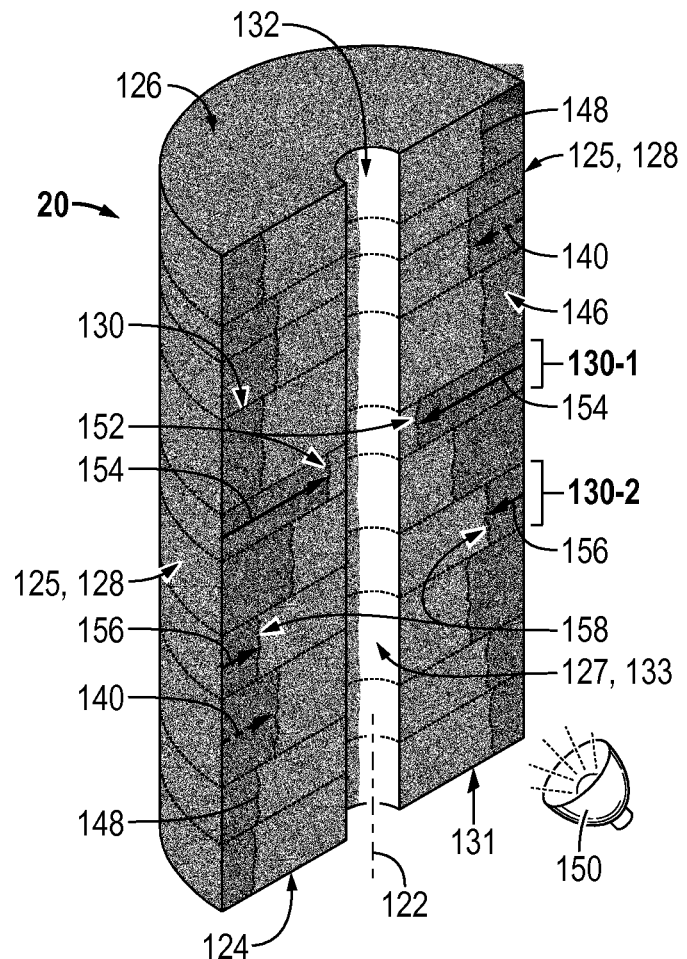
FIG. 7 illustrates a test fluid exposed core sample according to FIGS. 3 and 5 split along a plane perpendicular to the bedding planes according to one or more aspects of the disclosure.

Upon termination of the flow of test fluid, core sample 20 is removed from the test apparatus for analysis. The tested core sample that has been exposed to the test fluid is split, e.g., cut, along a plane 131 (splitting plane) perpendicular to the bedding planes of interest as illustrated for example in FIGS. 6 and 7. FIG. 6 illustrates the tested or exposed core sample 20 of FIGS. 2 and 4 split along a plane perpendicular to the bedding planes and FIG. 7 illustrates the tested or exposed core sample 20 of FIGS. 3 and 5 split along a plane perpendicular to the bedding planes. The resulting cross section is then inspected, for example under black light, revealing a flow field 146 and a fluorescent interface 148 identifying the invasion depth of the test fluid. The flow field 146 is permeated by the inflow of test fluid 140 extending from the inflow surface 125 to the invasion depth illustrated by the fluorescent interface 148.

The flow field 146 identifies local, on a scale of millimeters to inches, permeability variations in the core sample. The greater the invasion depth or length of test fluid 140, as shown by the separation of interface 148 from the inflow surface, identifies higher permeability. For example, a core sample may exhibit, on average, a permeability of 100 mD (millidarcy). However, analysis of the tested core sample can reveal local variations approximately equal to that average, above that average, and below that average. This type of localized information can assist an operator to optimize well inflow for example by designing a perforating strategy or other stimulation procedures. The flow field may be more detectable using a tracer, such as a fluorescent dye, within the test fluid 140. When a fluorescent dye is used, visibility of the flow field can be improved by exposing the tested core sample 20 to an ultraviolet light source 150, for example.

In FIG. 7, the flow field 146 is generally mirrored about the central axis 122 of the core sample 20. Mirroring of the flow field 146 indicates that fluid inflow was relatively uniform along the bedding layers; that is that inflow for a given layer is roughly uniform. This may not always be the case, as permeability within a core sample may vary within bedding layers due to composition of the core sample.

Qualitative and quantitative analysis of the core sample 20 can be accomplished by analyzing the invasion depth of the test fluid 140. Qualitative analysis can be made by simple comparison of the test fluid 140 invasion depth or inflow depth (interface 148) across the tested core sample 20. The variations in invasion depth of the fluorescence correlate with local permeability variations. For example, peaks 152 represent the highest permeability of the tested core sample 20. A qualitative analysis of the permeability at peaks 152 can be made by comparing a depth 154 at peaks 152 to other areas of the tested core sample 20; the invasion depth of the fluid saturation being the distance from the inflow surface 125. It can be seen that the depth 154 is significantly greater than the depth 156 at peaks 158 corresponding to a greater permeability in the layer 130-1 than the permeability of layer 130-2.

The absolute local permeability of each layer, e.g., layers 130-1, 130-2, etc., can be quantified, by taking into account the larger scale macroscopic average permeability of the tested core sample. For example, consider Darcy's law as applied relating the average permeability (kavg) to total flow rate (Qtot) of the test fluid, pressure drop across the tested core sample (ΔP), and the tested core sample dimensions, flowing length L and cross-sectional area (Atot):

$$Q_{tot} = \frac{k_{avg} A_{tot}}{\mu} \frac{\Delta P}{L} \qquad \text{Equation 1}$$

When analyzing multiple parallel layers, i.e. bedding planes, aligned in the flow direction, each cross sectional area Ai and local permeability ki, and quantity of layers "n", Equation 1 can be rewritten as:

$$Q_{tot} = \frac{\Delta P}{L\mu} \int_{i=1}^{n} k_i A_i \qquad \text{Equation 2}$$

Setting Equation 1 and Equation 2 equal to one another yields:

$$k_{avg} A_{tot} = \int_{i=1}^{n} k_i A_i \qquad \text{Equation 3}$$

Therefore, if each of the average permeability (kavg) of the tested core sample, the cross-sectional area of each bedding layer (Ai), and the relative permeability of each bedding layer are qualitatively known as described above, then the absolute permeability of each layer ki can be determined using Equation 3. Using this quantitative analysis, a more precise analysis of a reservoir surrounding a wellbore can be determined compared to the qualitative analysis.

Figure 8:
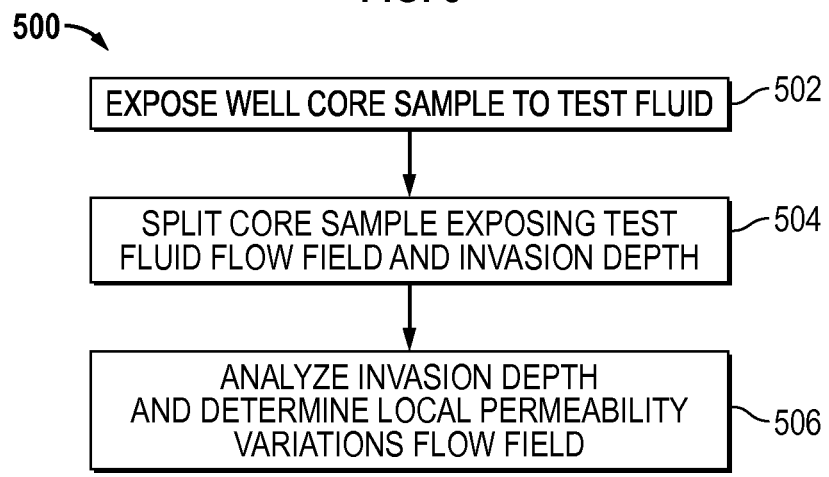
FIG. 8 is a flow diagram of a method of analyzing permeability of a well core according to one or more aspects of the disclosure.

FIG. 8 illustrates a method, generally denoted by the numeral 500, of analyzing a core sample. Method 500 is now described with reference to FIGS. 1-8. A core sample 20 is exposed at block 502 to a test fluid 140 containing a material or tracer, for example by flowing the test fluid in the direction from an inflow surface 125 to an exit surface 127. The test fluid may be a light mineral oil, a water/brine mix, or other fluid. The tracer provides enhanced detection of a flow field 146 of the test fluid and the length or depth of the flow field. The tracer may be, for example, a fluorescent dye that glows when exposed to an ultraviolet light source 150, a radioactive particle, or other chemical that permits enhanced visibility of the flow field 146. The test fluid flows parallel to the primary bedding plane 130 of the core sample 20 and from an inflow surface 125 toward an outflow surface 127. Exposure to the test fluid is terminated after a period of time, for example when the test fluid breaks through the exit surface 127 of the core sample. The exposed core sample 20 is then split, for example along a plane 131 perpendicular to the bedding plane 130, exposing a flow field 146 and depth of invasion (interface 148) of the test fluid (block 504). The permeability of the core sample 20 may then be quantitatively and qualitatively analyzed utilizing the flow field. In accordance to embodiments, variations in the local (i.e., within a few millimeters or inches) permeability of the core sample is determined.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A method, comprising:
    flowing a test fluid from an inflow surface of a core sample toward an exit surface of the core sample for a period of time;
    after the period of time, splitting the core sample along a splitting plane revealing an invasion depth of the test fluid from the inflow surface into the core sample; and
    determining local permeability variations in the core sample using the invasion depth.

2. The method of claim 1, wherein the test fluid is flowed parallel to a bedding plane of the core sample.

3. The method of claim 1, wherein the determining the local permeability variations comprises comparing the invasion depth at a first layer of the core sample to the invasion depth at a second layer of the core sample.

4. The method of claim 1, wherein the determining the local permeability variations comprises determining an absolute permeability of a first layer and an absolute permeability of a second layer of the core sample.

5. The method of claim 1, wherein the test fluid comprises a fluorescent material and further comprising enhancing visibility of the invasion depth by exposing the splitting plane to an ultraviolet light.

6. The method of claim 1, wherein the test fluid comprises a fluorescent material and the test fluid is flowed linearly parallel to a bedding plane of the core sample, and further comprising:
    enhancing visibility of the invasion depth by exposing the splitting plane to an ultraviolet light; and
    the determining the local permeability variations comprises determining an absolute permeability of a first layer and determining an absolute permeability a second layer of the core sample.

7. A method of analyzing a core sample from a wellbore, comprising:
    placing a core sample into a test cell, the core sample comprising first and second axial ends and an outer circumferential surface;
    flowing a test fluid from an inflow surface of the core sample toward an exit surface of the core sample for a period of time, wherein the first axial end is the inflow surface and the second axial end is the exit surface;
    after the period of time, splitting the core sample along a splitting plane revealing an invasion depth of the test fluid from the inflow surface into the core sample; and determining local permeability variations in the core sample using the invasion depth.

8. The method of claim 7, comprising terminating the flowing the test fluid when the test fluid breaks through the exit surface.

9. The method of claim 7, wherein the test fluid is flowed parallel to a bedding plane of the core sample.

10. The method of claim 7, wherein the determining the local permeability variations comprises comparing the invasion depth at a first layer of the core sample to the invasion depth at a second layer of the core sample.

11. The method of claim 7, wherein the determining the local permeability variations comprises determining an absolute permeability of a first layer and an absolute permeability of a second layer of the core sample.

12. The method of claim 7, wherein the test fluid comprises a fluorescent material and further comprising enhancing visibility of the invasion depth by exposing the splitting plane to an ultraviolet light.

13. The method of claim 7, wherein the test fluid comprises a fluorescent material and the test fluid is flowed linearly parallel to a bedding plane of the core sample, and further comprising:
   enhancing visibility of the invasion depth by exposing the splitting plane to an ultraviolet light; and
   the determining the local permeability variations comprises determining an absolute permeability of a first layer and determining an absolute permeability a second layer of the core sample.

14. A method of analyzing a core sample from a wellbore, comprising:
   placing a core sample into a test cell, the core sample comprising first and second axial ends, an outer circumferential surface, and an axial channel having an inner surface;
   flowing a test fluid from an inflow surface of the core sample toward an exit surface of the core sample for a period of time, wherein the inflow surface is one of the outer circumferential surface and the inner surface and the exit surface is the other of the outer circumferential surface and the inner surface;
   after the period of time, splitting the core sample along a splitting plane revealing an invasion depth of the test fluid from the inflow surface into the core sample; and
   determining local permeability variations in the core sample using the invasion depth.

15. The method of claim 14, wherein the test fluid is flowed parallel to a bedding plane of the core sample.

16. The method of claim 14, wherein the determining the local permeability variations comprises comparing the invasion depth at a first layer of the core sample to the invasion depth at a second layer of the core sample.

17. The method of claim 14, wherein the determining the local permeability variations comprises determining an absolute permeability of a first layer and an absolute permeability of a second layer of the core sample.

18. The method of claim 14, wherein the test fluid comprises a fluorescent material and further comprising enhancing visibility of the invasion depth by exposing the splitting plane to an ultraviolet light.

19. The method of claim 14, wherein the test fluid comprises a fluorescent material and the test fluid is flowed linearly parallel to a bedding plane of the core sample, and further comprising:
   enhancing visibility of the invasion depth by exposing the splitting plane to an ultraviolet light; and
   the determining the local permeability variations comprises determining an absolute permeability of a first layer and determining an absolute permeability a second layer of the core sample.

20. The method of claim 19, wherein the test fluid is flowed parallel to a bedding plane of the core sample; and the splitting plane is substantially parallel to the bedding plane.

\* \* \* \* \*